(12) United States Patent  (10) Patent No.: US 8,919,282 B2
Jardine  (45) Date of Patent: Dec. 30, 2014

(54) SYSTEM AND METHOD FOR CONTINUOUS VERMICULTURE CYCLE

(75) Inventor: Miguel Jardine, Phoenix, AZ (US)

(73) Assignee: The Local Soil Company, LLC, Phoenix, AZ (US)

( * ) Notice: Subject to any disclaimer, the term of this patent is extended or adjusted under 35 U.S.C. 154(b) by 110 days.

(21) Appl. No.: 13/336,037

(22) Filed: Dec. 23, 2011

(65) Prior Publication Data

US 2012/0234244 A1   Sep. 20, 2012

Related U.S. Application Data

(60) Provisional application No. 61/426,682, filed on Dec. 23, 2010.

(51) Int. Cl.
A01K 29/00 (2006.01)
A01G 9/00 (2006.01)
A01K 67/033 (2006.01)

(52) U.S. Cl.
CPC .............. *A01K 67/0332* (2013.01); *A01G 9/00* (2013.01)
USPC ........................................................ 119/6.7

(58) Field of Classification Search
USPC ................. 119/6.7; 47/59 R, 62 R, 62 N, 63
See application file for complete search history.

(56) References Cited

U.S. PATENT DOCUMENTS

| | | | | |
|---|---|---|---|---|
| 3,635,816 A | * | 1/1972 | Golub | 210/602 |
| 4,194,320 A | * | 3/1980 | Svirklys | 47/59 R |
| 4,262,633 A | * | 4/1981 | Taboga | 119/6.7 |
| 4,334,386 A | * | 6/1982 | Burcombe et al. | 47/62 E |
| 4,397,114 A | * | 8/1983 | Skaife | 47/81 |
| 4,513,685 A | * | 4/1985 | Frijters et al. | 119/6.7 |
| 4,754,571 A | * | 7/1988 | Riechmann | 47/59 R |
| 6,576,462 B2 | | 6/2003 | Thompson | |
| 6,890,438 B2 | | 5/2005 | Shankar et al. | |
| 7,018,831 B2 | | 3/2006 | Gitt | |
| 7,226,240 B2 | | 6/2007 | Tyler | |
| 7,452,165 B2 | | 11/2008 | Tyler | |
| 7,604,742 B2 | | 10/2009 | Shankar et al. | |
| 2003/0059931 A1 | | 3/2003 | Gitt | |
| 2005/0090405 A1 | | 4/2005 | Growcock et al. | |
| 2005/0133442 A1 | | 6/2005 | Koehler | |
| 2007/0224004 A1 | | 9/2007 | Tyler | |
| 2007/0253785 A1 | | 11/2007 | Tyler | |
| 2008/0016759 A1 | | 1/2008 | Tyler | |
| 2010/0199734 A1 | | 8/2010 | Bottcher et al. | |

FOREIGN PATENT DOCUMENTS

| | | |
|---|---|---|
| EP | 0999194 | 5/2000 |
| KR | 20100016710 | 2/2010 |
| WO | 9526943 | 10/1995 |
| WO | WO-2010/096107 A2 | 8/2010 |

* cited by examiner

*Primary Examiner* — Kristen C Hayes
(74) *Attorney, Agent, or Firm* — Tarolli, Sundheim, Covell & Tummino LLP (57) ABSTRACT

A method for continuous vermiculture is provided. The method includes providing a continuous vermiculture culture system. The continuous vermiculture culture system includes at least one culture member that is fluidly connected to an irrigation system. After preparing a feeding solution, a volume of the feeding solution is then infused into the at least one culture member via the irrigation system. The steps of providing a feeding solution and infusing a volume of the feeding solution into the at least one culture member via the irrigation system are optionally repeated to promote formation of culture-grade soil and plant growth within the at least one culture member.

5 Claims, 5 Drawing Sheets

SYSTEM AND METHOD FOR CONTINUOUS VERMICULTURE CYCLE

RELATED APPLICATION

This application claims the benefit of U.S. Provisional Patent Application Ser. No. 61/426,682, filed Dec. 23, 2010, which is hereby incorporated by reference in its entirety for all purposes.

TECHNICAL FIELD

The present invention relates generally to a system and method for processing organic waste into a liquid solution to grow organic crops, and more particularly to a continuous vermiculture system and related cycle for producing culture-grade soil and growing plants.

BACKGROUND OF THE INVENTION

Organic matter is the vast array of carbon compounds in soil. It is originally created by plants, microbes and other organisms. These compounds play a variety of roles in nutrient, water, and biological cycles. Organic matter covers a wide range of things, such as lawn clippings, leaves, stems, branches, moss, algae and lichens, parts of animals, manure droppings, sewage sludge, sawdust, insects, earthworms and microbes. Organic matter increases the nutrient holding capacity of soil. It serves as a pool of nutrients for plants and chelates nutrients, preventing the nutrients from becoming permanently unavailable to the plants. It is food for soil organisms, which hold onto the nutrients and release them in a form that is readily available to plants. Additionally, organic matter improves the water dynamics of soil and affects soil structure by reducing crusting and encouraging root development and aggregation.

The loss of organic matter from soil, also known as soil depletion, occurs when the components that contribute to fertility are removed and not replaced, and the conditions that support soil fertility are not maintained. Soil depletion can then lead to poor crop yields. In agriculture, for example, depletion can be due to excessively intense cultivation and inadequate soil management. Depletion may also occur through a variety of other effects, including overtillage (which damages soil structure), overuse of inputs, such as synthetic fertilizers and herbicides (which leave residues and buildups that inhibit microorganisms), and salinization of soil.

SUMMARY OF THE INVENTION

According to one aspect of the present invention, a method for continuous vermiculture is provided. The method includes providing a continuous vermiculture culture system. The continuous vermiculture culture system includes at least one culture member that is fluidly connected to an irrigation system. After preparing a feeding solution, a volume of the feeding solution is infused into the at least one culture member via the irrigation system. The steps of providing a feeding solution and infusing a volume of the feeding solution into the at least one culture member via the irrigation system are optionally repeated to promote formation of culture-grade soil and plant growth within the at least one culture member.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
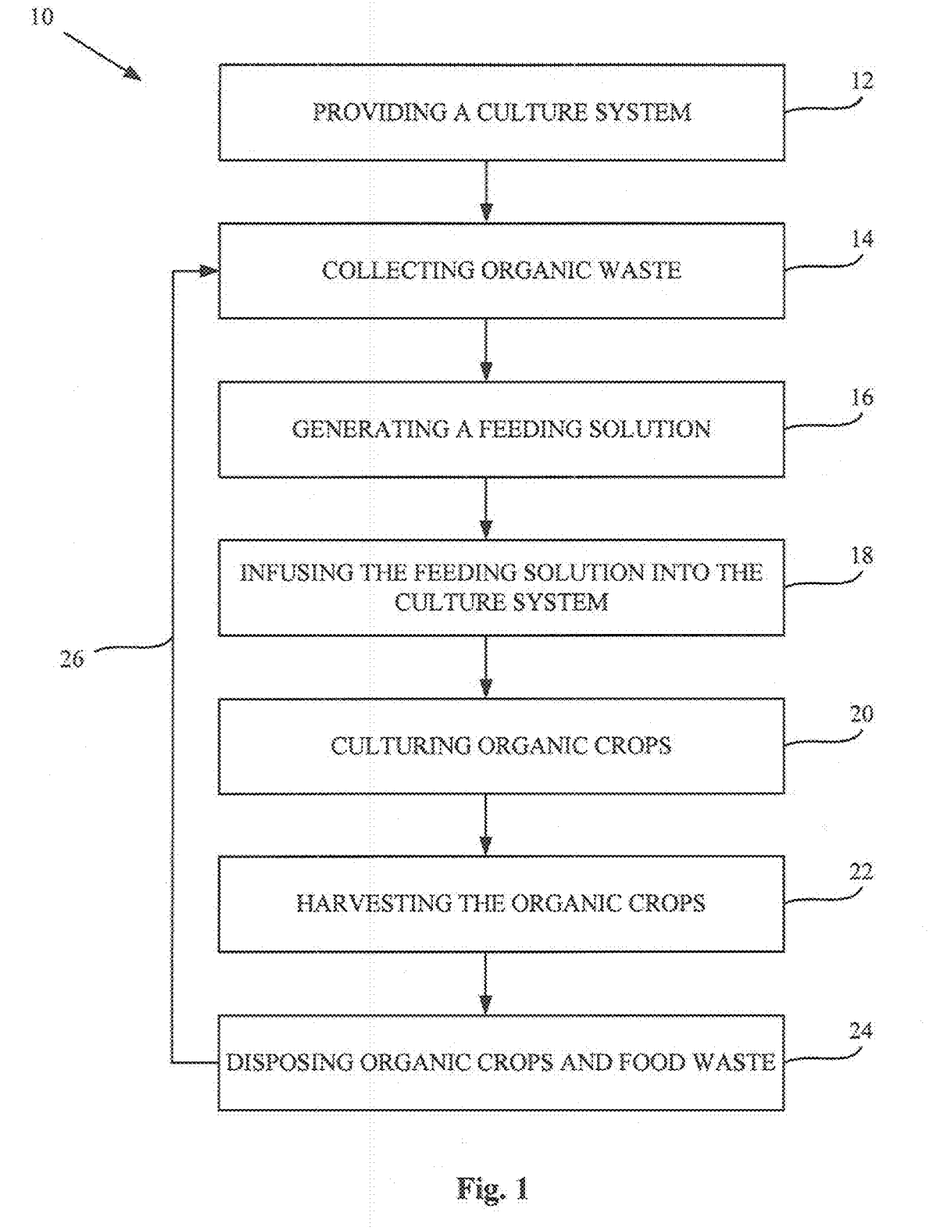
FIG. 1 is a process flow diagram illustrating a method for a continuous vermiculture cycle according to one aspect of the present invention.

The present invention relates generally to a system and method for processing organic waste into a liquid solution to grow organic crops, and more particularly to a continuous vermiculture system and related cycle for producing culture-grade soil and growing plants. As representative of one aspect of the present invention, FIG. 1 illustrates a method 10 for a continuous vermiculture cycle for producing culture-grade soil and/or growing organic crops. The present invention harvests the regenerative power of nature by converting consumable organic waste (e.g., food waste) by-products into lush organic growth. Unlike conventional vermiculture systems and methods, which are eventually depleted of the minerals and nutrients needed to sustain the earthworm inhabitants, the present invention supplies earthworms with a liquid effluent of organic waste by-products so that the earthworms continuously create the needed nutrients to grow lush organic crops in any environment.

In one aspect of the method 10, a continuous vermiculture system 30 (FIG. 2) is provided at Step 12. The continuous vermiculture system 30 comprises at least one culture member 32 that is fluidly connected to an irrigation system 34. The irrigation system 34 generally comprises the following components: at least one source 36 of a feeding solution; at least one primary fluid line 38 that is fluidly connected to the source of the feeding solution; at least one junction member 40 that fluidly joins the primary fluid line and at least one secondary fluid line 42; and at least one tertiary fluid line 44 that is fluidly connected between the culture member and the secondary fluid line. Additional or optional components of the irrigation system 34 can include one or more pumps 46, one or more pressure gauges (not shown), one or more fluid flow control switches (not shown) (e.g., timed valves), one or more fluid flow sensors (not shown), one or more fluid quality sensors (not shown), and one or more central fluid flow controllers (not shown) for automated and/or centralized control of the continuous vermiculture system 30.

Figure 2:
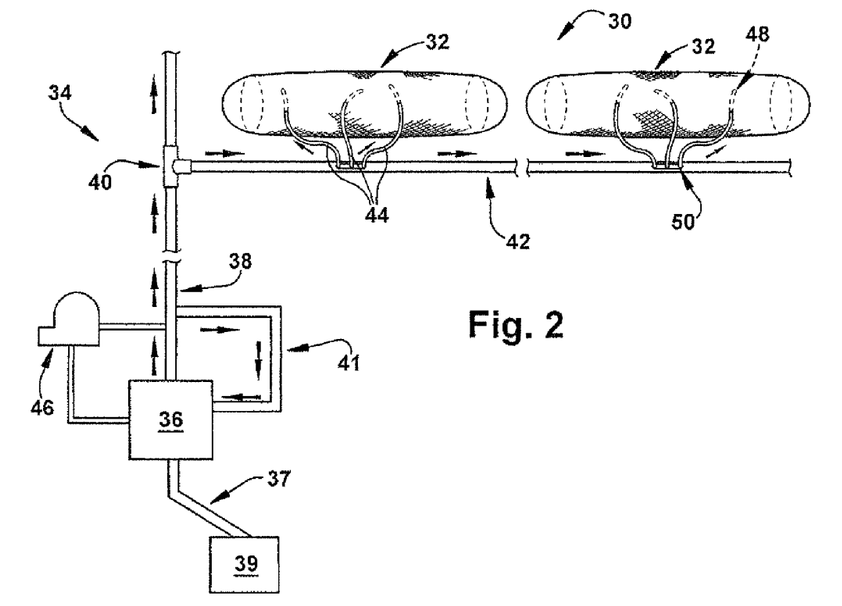
FIG. 2 is a schematic diagram illustrating a continuous vermiculture system constructed in accordance with another aspect of the present invention.

The source 36 of the feeding solution can include any device or structure (e.g., a vat or tank) capable of holding a volume of feeding solution (described in more detail below). The feeding solution is supplied to the source 36 via a conduit 37 that is fluidly connected to a device or system 39 capable of generating the feeding solution. Alternatively, the feeding solution can be manually supplied to the source 36 (e.g., by loading a pre-determined volume into the source as needed). In one example of the present invention, the device or system 39 can comprise a commercially-available food waste decomposer, such as the ORCA GREEN bioreactor (Orca Green, LLC, Marietta, Ga.). Other examples of devices and systems for decomposing organic food waste into a liquid effluent are known in the art. The device or system 39 is capable of decomposing organic waste (e.g., food waste, organic crop waste, lawn clippings, bark, leaves, branches, etc.) into a liquid effluent, which can then be fortified with one or more additives to form the feeding solution. Prior to supplying the source 36, for example, the liquid effluent generated by the device or system 39 can be supplied with at least one additive, such as a probiotic (e.g., *Lactobacillus*), sands or clays, fish emulsion, magnesium, nitrogen, phosphorus, potassium, calcium and iron. Such additives can be useful in increasing the oxygen content and general organic health of the culture members 32.

It will be appreciated that the liquid effluent can be fortified (i.e., to form the feeding solution) at one or a variety of time points. For example, the liquid effluent can be fortified during decomposition of food waste, after generation of the liquid effluent but prior to transfer to the source 36, or after the liquid effluent has been delivered to the source. It will also be appreciated that the amount and combination of additives used to fortify the liquid effluent, and thus form the feeding solution, can be tailored depending upon the particular application of the continuous vermiculture system 30. For example, the amount and type of additive(s) used to form the feeding solution can be adjusted depending upon the particular type of organic crop desired and/or the ambient growing conditions (e.g., arid, humid, etc.).

The source 36 of the feeding solution is fluidly connected to the primary fluid line 38. The primary fluid line 38 comprises any conduit capable of flowing the feeding solution therethrough. The primary fluid line 38 can have any length and diameter, depending upon the particular application of the continuous vermiculture system 30. The primary fluid line 38 can be rigid, semi-rigid, or supple and, depending upon the particular configuration of the continuous vermiculture system 30, can be made of metal, a metal alloy, plastic, or a combination thereof. Also connected to the source 36 and the primary fluid line 38 is a return line 41 that can be used to continuously circulate and stir the feeding solution in the source.

As shown in FIG. 2, the primary fluid line 38 is fluidly connected to the secondary fluid line 42 via a junction member 40. The junction member 40 can have a T-shaped configuration and be made of a suitable material, such as a metal, a metal alloy, plastic, or a combination thereof. It will be appreciated that the junction member 40 can have any suitable size and/or shape, depending upon the particular configuration of the continuous vermiculture system 30. It will also be appreciated that the junction member 40 can include any number of valves (not shown) for controlling or adjusting fluid flow.

The secondary fluid line 42 is fluidly connected to the junction member 40 and generally comprises any conduit capable of flowing the feeding solution therethrough. The secondary fluid line 42 can be rigid, semi-rigid, or supple and, depending upon the particular configuration of the continuous vermiculture system 30, can be made of metal, a metal alloy, plastic, or a combination thereof. In one example of the present invention, the secondary fluid line 42 can have a diameter that is less than the diameter of the primary fluid line 38. The decreased diameter of the secondary fluid line 42 can provide increased fluid pressure within the secondary fluid line. It will be appreciated that the secondary fluid line 42 can have any length and diameter, depending upon the particular application of the continuous vermiculture system 30.

Each of the tertiary fluid lines 44 includes oppositely disposed first and second ends 48 and 50 that are fluidly connected to each of the culture members 32 and the secondary fluid line 42, respectively. The tertiary fluid lines 44 generally comprise any conduit capable of flowing the feeding solution therethrough. The tertiary fluid lines 44 can be rigid, semi-rigid, or supple and, depending upon the particular configuration of the continuous vermiculture system 30, can be made of metal, a metal alloy, plastic, or a combination thereof. Although three tertiary fluid lines 44 are connected to each of the culture members 32 in FIG. 2, it will be appreciated that a fewer or greater number of tertiary fluid lines can be connected to one or more of the culture members. The tertiary fluid lines 44 can have any length and diameter desired. In one example of the present invention, the tertiary fluid lines 44 can have a diameter that is less than the diameter of the secondary fluid line 42 to provide increased fluid pressure within each of the tertiary fluid lines.

As shown in FIG. 2, the first end 48 of each of the tertiary fluid lines 44 partially extends into each of the culture members 32. Positioning the first end 48 of each of the tertiary fluid lines 44 in each of the culture members 32 helps facilitate widespread delivery of the feeding solution within the culture members. It will be appreciated, however, that the first end 48 of each of the tertiary fluid lines 44 may be flush-mounted to each of the culture members 32. Additionally, it will be appreciated that the tertiary fluid lines 44 can be fluidly connected to each of the culture members 32 in any desired pattern or configuration (e.g., symmetrically or asymmetrically spaced apart).

Figure 3A:
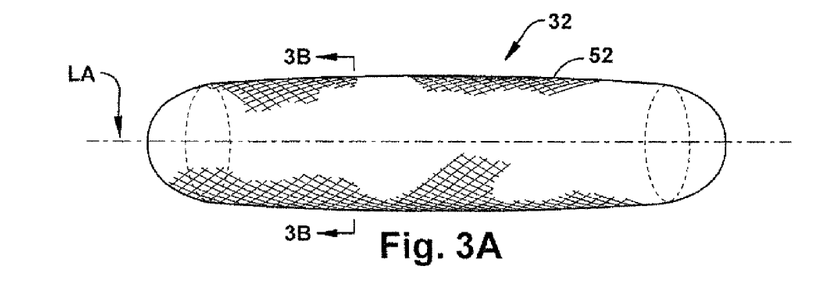
FIG. 3A is a perspective view of a culture member comprising one component of the continuous vermiculture system in FIG. 2.
Figure 3B:
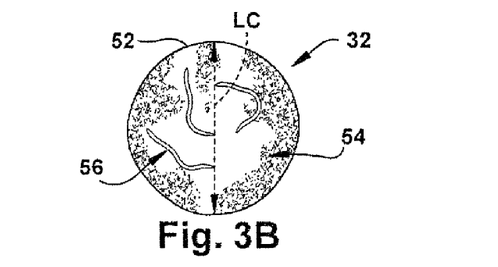
FIG. 3B is a cross-sectional view taken along Line 3B-3B in FIG. 3A.

Referring to FIGS. 3A-B, each of the culture members 32 generally comprises an elongate mesh enclosure 52 that is formed from a mesh or netting-like material and includes a filler material 54 surrounded by the mesh enclosure. Each of the culture members 32 has a tube-like configuration defining a longitudinal axis LA and a longitudinal cross-section LC. The longitudinal cross-section LC can resemble any closed shape, such as a circle, a non-circle (e.g., an oval), and/or a polygon (e.g., a triangle, rectangle, square, hexagon, the shape of the letter "D", etc.). The particular dimensions of the culture members 32, such as length, width, cross-sectional area, etc., can be varied as needed. That is, the dimensions of one or more of the culture members 32 can be scaled up or down depending upon the particular application of the continuous vermiculture system 30.

The material used to form the mesh enclosure 52 can be fabricated from a flexible netting material, which can be woven, sewn, knitted, welded, molded, and/or extruded, etc. One example of a mesh enclosure 52 that may be used to form the culture members 32 is disclosed in U.S. Pat. No. 7,226, 240 to Tyler, the entirety of which is hereby incorporated by reference. Briefly, the material used to form the mesh enclosure 52 can be biodegradable, such as cotton, a natural fiber, UV-sensitive plastic, and/or biodegradable polymer (e.g., starch) that can biodegrade at a predetermined rate. Alternatively, all and/or any portion of the material used to form the mesh enclosure 52 can resist biodegradation. For example, the material can be fabricated from plastic, UV-inhibited plastic, polyester, polypropylene, multi-filament polypropylene, polyethylene, LDPE, HDPE, rayon, and/or nylon. The material used to form the mesh enclosure 52 can be of any diameter and/or thickness. The material can have any mesh opening pattern, such as diamond, hexagonal, oval, round, and/or square, etc. Any number of mesh enclosures 52 can be coupled together in a process called "sleeving" to form a continuous mesh tube (and/or mesh sheet, not shown) of any size.

The filler material 54 can partially or completely fill each of the culture members 32. The filler material 54 can include one or a combination of materials, such as compost, composted products, mulch, sawdust, soil, gravel and/or various other organic and/or inorganic substances. As shown in FIG. 3B and described in more detail below, the filler material 54 includes one or more earthworms 56. Advantageously, the earthworms 56 can continuously create and replenish the nutrients needed for sustainable plant growth.

The filler material 54 can comprise any of a number of materials including, but not limited to, compost, composted organic materials, organic feedstocks, composted products, mulch, wood shavings, lime, clay, pea gravel, gravel, sand, soil, wood chips, bark, pine bark, peat, soil blends, straw, hay, leaves, sawdust, paper mill residuals, wood wastes, wood pellets, hemp, bamboo, biosolids, coconut fibers, coir, wheat straw, rice straw, rice hulls, corn husks, corn, grain, corn stalks, oat straw, soybean hulls, palm wastes, palm leaves, agricultural waste products, manure, wool, hair, sugar cane bagasse, seed hulls, jute, flax, hulls, organic waste, cat litter, activated charcoal, diatomaceous earth, chitin, ground glass, alum, aluminum oxide, alum sludge, iron oxide, iron ore, iron ore waste, ironite, iron sulfate, pumice, perlite, rock fragments, mineral fragments, ion exchange substances, resin, and/or beads, zeolites, plant seeds (e.g., fruit and vegetable seeds), plugs, sprigs, spores, mycorrhizae, humic acid, and/or biological stimulants, microorganisms, microflora, rhizospheres, mycospheres, and/or ecosystems, etc.

The earthworms 56 included as part of the filler material 54 can include any member of the phylum Annelida. For example, the earthworms 56 can include any member of the phylum Annelida that is capable of burrowing through soil and consuming organic matter therein to promote mineralization and nutrient uptake by vegetation. In one example of the present invention, one or more of the earthworms 56 can include an epigeic earthworm, such as *Eisenia fetida*. The earthworms 56 comprising the filler material 54 can be of the same or different genus/species. For example, the particular genus/species of earthworm 56 included in the filler material 54 can be selected based on the type of climate or environment (e.g., arid, humid, etc.) in which the continuous vermiculture system 30 will be used. It will be appreciated that any desired number of earthworms 56 having the same or different sizes can be included in the filler material 54.

It will also be appreciated that the continuous vermiculture system 30 can be scaled to include a greater or fewer number of culture members 32 as those shown in FIG. 2. For backyard applications, for instance, the continuous vermiculture system 30 may include only one culture member 32 having a length of about 3 feet and a diameter of about 8 inches. Alternatively, for commercial agriculture applications, the continuous vermiculture system 30 can include ten, twenty, or even more culture members 32 and be spread across a desired parcel of land (e.g., one acre of land). In another example, the continuous vermiculture system 30 can be configured for optimal plant production in an urban environment. Moreover, the continuous vermiculture system 30 is highly scalable and can be adapted for optimal plant production in any environment.

Figure 5:
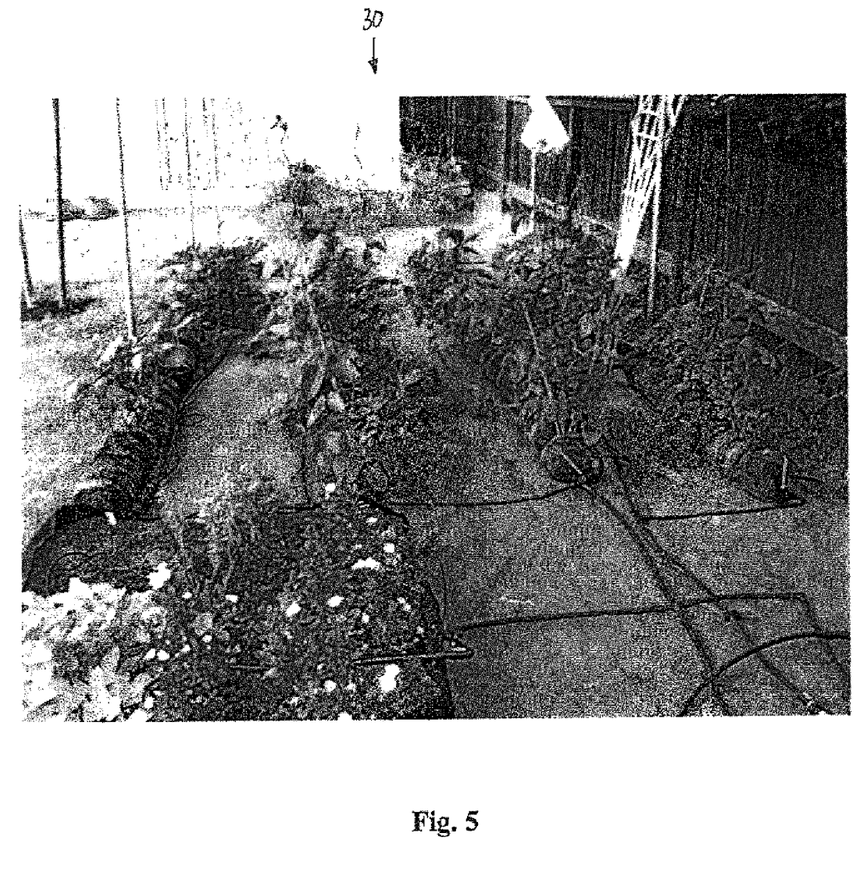
FIG. 5 is an image showing organic crops about 6 weeks after seeding in the continuous vermiculture system of FIG. 4.

Although the culture members 32 are illustrated and described herein as having a tube-like configuration, it will be appreciated that the culture members can comprise any type of container or apparatus that is capable of housing the filler material 54 and being fluidly connected to the irrigation system 34. For example, a culture member 32 can comprise an open container that is filled with a filler material 54 (e.g., including earthworms 56 and cocopeat) and is fluidly connected to the irrigation system 34. One example of such an open container is shown in FIG. 5 (bottom left-hand corner) and is commercially-available as the MEADOW (Woolly Pocket, Inc., Phoenix, Ariz.).

Either prior to, during, or after provision of the continuous vermiculture system 30, organic waste (e.g., food waste) is collected at Step 14. Organic waste, such as food waste can be collected from any one or combination of sources, such as restaurants, hotels, schools, cafeterias, etc. Organic food waste can include any type of consumable food by-product, such as vegetables, meats, grains, pasta, bread, fruits, etc., that has been disposed of. The amount of organic waste collected will depend upon the particular application for which the method 10 is intended.

After collecting an amount of the organic waste, the organic waste is disposed in a device or system capable of decomposing the organic waste into a liquid effluent (i.e., feeding solution) (Step 16). Using the ORCA GREEN bioreactor, for example, wasted fruit and vegetable scraps can be loaded into the bioreactor. Taking advantage of low temperature composting and environmentally friendly microorganisms, the organic food waste is composted until only liquid effluent (e.g., water) and carbon dioxide are produced. The liquid effluent (or feeding solution) is then collected and prepared for further use.

At Step 18, the feeding solution is fed into the irrigation system 34. As indicated by the arrows in FIG. 2, the feeding solution is flowed through the source 36 via the primary fluid line 38 into the junction member 40, through the secondary fluid line 42, and then into each of the culture members 32 via the tertiary fluid lines 44. The rate and amount of the feeding solution delivered to the culture members 32 can depend on a number of factors including, but not limited to, the size and number of culture members, the type of organic crop(s) being cultured, the dimensions of the primary, secondary and tertiary fluid lines 38, 42 and 44, and the climate or environment in which the continuous vermiculture system 30 is located. For example, an arid environment may require a greater flow rate to prevent the filler material 54 from drying out.

The feeding solution can be flowed through the irrigation system 34 continuously and/or intermittently. The continuous vermiculture system 30 can be configured as a closed-loop system so, for example, the feeding solution is continuously flowed therethrough. Alternatively, the continuous vermiculture system 30 can be configured so that a desired amount of the feeding solution is delivered to one or more of the culture members 32 at specific time intervals. The feeding solution can be flowed through the irrigation system 34 via one or more pumps 46 or via a gravity-based mechanism (not shown). The feeding solution can be delivered to the culture members 32 one at a time, all at once, or a combination thereof (e.g., in a select pattern).

Figure 4:
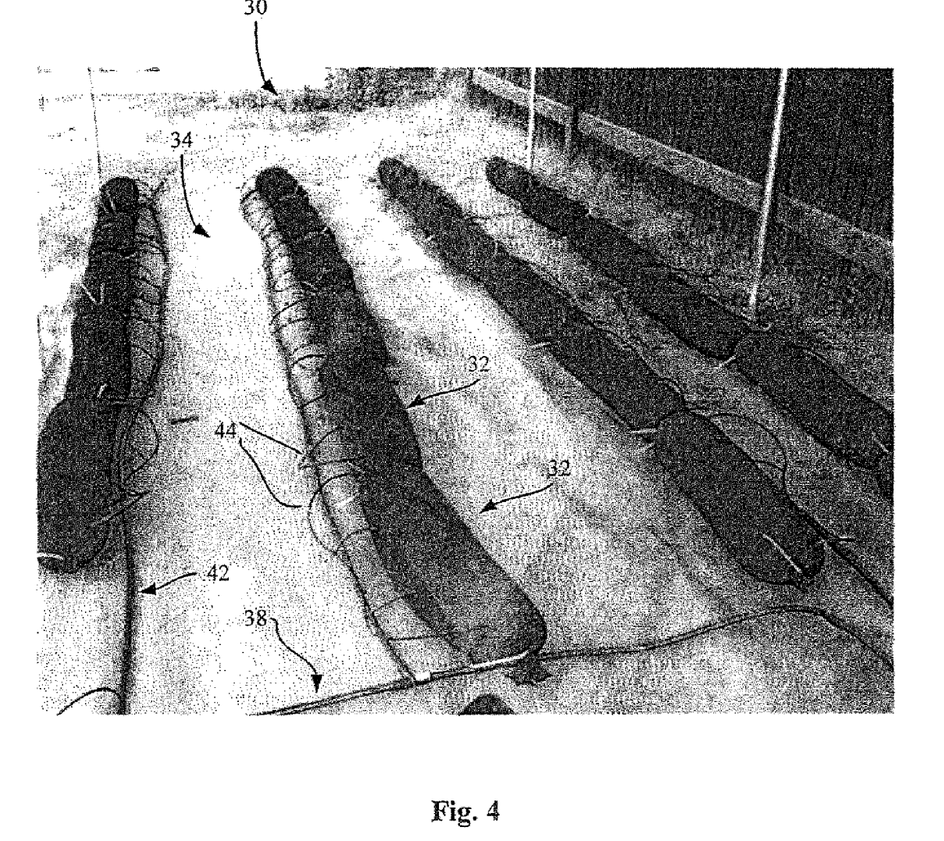
FIG. 4 is an image showing the continuous vermiculture system in FIG. 2 before initial seeding.
Figure 6:
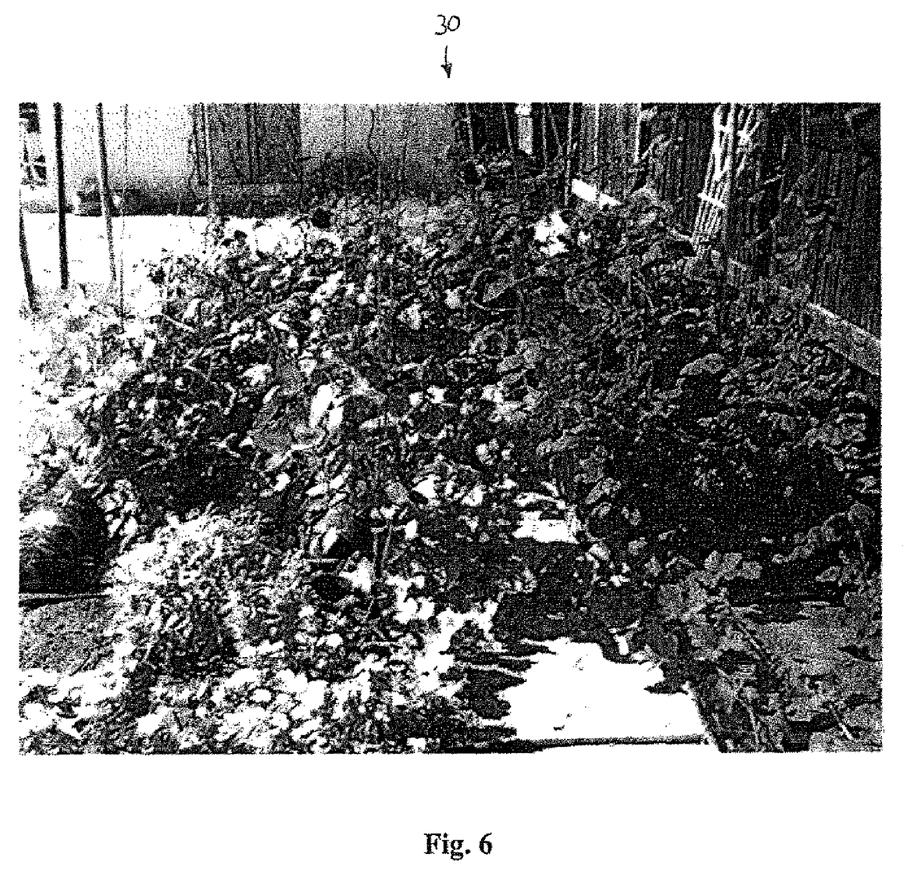
FIG. 6 is an image showing the organic crops in FIG. 5 about 10 weeks after seeding in the continuous vermiculture system of FIG. 4.

If it has not been done so already, one or more seeds of a desired plant (or plants) can be planted within each of the culture members 32 (FIG. 4). At Step 20, the culture members 32 are cultured by exposing the culture members to an appropriate amount of light and then infusing the appropriate amount of feeding solution into the culture members. Depending upon the type of plant(s) being cultured, all or only a portion of one or more of the culture members 32 can be exposed to partial or complete sunlight, for example. As shown in FIGS. 5-6, the culture members 32 are then cultured for an appropriate period of time until lush organic crop has been successfully cultured. At Step 22, the cultured organic crop can be harvested and consumed and/or converted into other non-food products, such as soaps, oils, medicines, etc.

After the organic crop is harvested and consumed, any organic waste (e.g., food waste and/or organic crops) can be disposed of at Step 24. To complete the virtuous cycle of the present invention, the organic waste can be recycled (Step 26) by depositing the organic waste into any device or system capable of decomposing the organic waste into a liquid effluent (feeding solution). Beginning at Step 14, the method 10 can then be repeated to once again culture organic crop that is ready for consumption. Not only are lush, healthy plants generated by the method 10, but so too is culture-grade soil that can be reused with the present invention or exported for other uses. Moreover, by generating a feeding solution from organic waste (e.g., organic food waste) to sustain the population of earthworms 56 in each of the culture members 32, the nutrients in the filling material are continuously regenerated to promote sustained and continuous plant growth.

From the above description of the invention, those skilled in the art will perceive improvements, changes and modifications. For example, other additives that can be included within the filler material 54 include fertilizers, pre-emergents, herbicides, nutrients, minerals, insecticides, pesticides, admixtures, aggregates, flocculants, polymers, chemical binders, and/or water absorbers, etc., chosen to enhance plant life. Additionally, it will be appreciated that the term "organic" as used herein is not restricted to "organically-certified" products or produce (as defined by the USDA, for example); rather, the term is intended to have its broadest meaning and include, for example, produce, crops, or food waste that includes carbon-containing compounds. Such improvements, changes, and modifications are within the skill of the art and are intended to be covered by the appended claims.

Having described the invention, the following is claimed:

1. A method for continuous vermiculture comprising:
   (a) providing a continuous vermiculture culture system, the continuous vermiculture culture system comprising at least one culture member, comprising at least one earthworm, that is fluidly connected to an irrigation system;
   (b) preparing a feeding solution, wherein the feeding solution comprises organic food waste;
   (c) infusing a volume of the feeding solution into the at least one culture member via the irrigation system; and
   (d) optionally repeating steps (b) and (c) to promote formation of culture-grade soil and plant growth within the at least one culture member; wherein said step of preparing a feeding solution further comprises the step of placing an amount of organic food waste into a device for decomposing the organic food waste into a liquid effluent.

2. The method of claim 1, wherein said step of providing a continuous vermiculture culture system further comprises providing the irrigation system including:
   at least one source of the feeding solution;
   at least one primary fluid line connected to the at least one source;
   at least one junction member connected to the at least one primary fluid line;
   at least one secondary fluid line connected to the at least one junction member; and
   at least one tertiary fluid line that extends between, and is fluidly connected to, the at least one culture member and the at least one secondary fluid line.

3. The method of claim 1, wherein the at least one culture member comprises a mesh enclosure that surrounds a filler material and the at least one earthworm.

4. The method of claim 3, wherein the filler material further comprises soil, seeds, and at least one of coconut shavings and probiotic.

5. A method for forming culture-grade soil that facilitates plant growth, comprising the steps of:
   decomposing an organic waste material into a liquid feeding solution;
   infusing a portion of the liquid feeding solution into a medium, wherein the medium comprises an earthworm; and
   forming the culture-grade soil based on the earthworm consuming at least a portion of the liquid feeding solution; wherein decomposing organic waste material into a feeding solution comprises placing an amount of organic food waste into a device for decomposing the organic good waste into a liquid effluent.

\* \* \* \* \*

UNITED STATES PATENT AND TRADEMARK OFFICE
CERTIFICATE OF CORRECTION

| | | |
|---|---|---|
| PATENT NO. | : 8,919,282 B2 | Page 1 of 1 |
| APPLICATION NO. | : 13/336037 | |
| DATED | : December 30, 2014 | |
| INVENTOR(S) | : Miguel Jardine | |

It is certified that error appears in the above-identified patent and that said Letters Patent is hereby corrected as shown below:

In the Claims

Column 8, line 27, Claim 4:   "probiotic" should be --probiotics--

Signed and Sealed this
Fifteenth Day of September, 2015

Michelle K. Lee
*Director of the United States Patent and Trademark Office*